(12) United States Patent
Choi et al.

(10) Patent No.: US 9,838,228 B2
(45) Date of Patent: Dec. 5, 2017

(54) DEVICE FOR REMOVING PARTIAL DISCHARGE NOISE AND METHOD OF DIAGNOSING THE SAME

(71) Applicant: Korea Electric Power Corporation, Seoul (KR)

(72) Inventors: Kwang Sik Choi, Daegu (KR); Jung Cheol Seo, Daegu (KR)

(73) Assignee: KOREA ELECTRIC POWER CORPORATION, Seoul (KR)

( * ) Notice: Subject to any disclaimer, the term of this patent is extended or adjusted under 35 U.S.C. 154(b) by 806 days.

(21) Appl. No.: 14/347,968

(22) PCT Filed: Sep. 28, 2012

(86) PCT No.: PCT/KR2012/007891
§ 371 (c)(1),
(2) Date: Mar. 27, 2014

(87) PCT Pub. No.: WO2013/048173
PCT Pub. Date: Apr. 4, 2013

(65) Prior Publication Data
US 2014/0233686 A1   Aug. 21, 2014

(30) Foreign Application Priority Data

Sep. 28, 2011 (KR) .................. 10-2011-0098383
Nov. 29, 2011 (KR) .................. 10-2011-0126368

(51) Int. Cl.
*H04L 25/08* (2006.01)
*G01R 31/12* (2006.01)
(Continued)

(52) U.S. Cl.
CPC ......... *H04L 25/08* (2013.01); *G01N 29/2418* (2013.01); *G01N 29/32* (2013.01);
(Continued)

(58) Field of Classification Search
CPC ............ G01R 31/1218; G01R 31/1272; G01R 31/14; G01N 29/2418; G01N 29/46;
(Continued)

(56) References Cited

U.S. PATENT DOCUMENTS

| | | | | |
|---|---|---|---|---|
| 5,680,059 A | * | 10/1997 | Shiota | G01R 31/1227 324/547 |
| 2008/0280578 A1 | * | 11/2008 | Nimura | H03F 1/342 455/249.1 |
| 2013/0006560 A1 | * | 1/2013 | Cern | G01R 31/1272 702/66 |

FOREIGN PATENT DOCUMENTS

| | | |
|---|---|---|
| JP | 05-019008 A | 1/1993 |
| KR | 10-2002-0023854 A | 3/2002 |

(Continued)

OTHER PUBLICATIONS

Nash, Ask the Applications Engineer-28:Logarithmic Amplifiers Explained, Mar. 1999, pp. 1-10.*

(Continued)

*Primary Examiner* — John Breene
*Assistant Examiner* — L. Anderson
(74) *Attorney, Agent, or Firm* — McDermott Will & Emery LLP

(57) ABSTRACT

There are provided a device for removing partial discharge noise and a method of diagnosing the same. The device includes a noise removing device configured to remove noise of a partial discharge signal using a reaction rate difference of signals when the partial discharge signal is generated, and output a signal in which noise is removed, a laser module configured to output a laser beam to a surface of a power device when the partial discharge signal is generated and extract sound wave and vibration data from a reflection signal of the laser beam, a correlation analyzing unit configured to compare the partial discharge signal in (Continued)

which noise is removed input through a sensor connecting unit and the sound wave and vibration data extracted through the laser module, and analyze a correlation, and a partial discharge diagnostic unit configured to perform partial discharge diagnosis on a signal that matches the partial discharge signal in which noise is removed with at least one of a generation cycle, a time, and a phase of the sound wave and vibration data based on a result of correlation analysis of the correlation analyzing unit.

9 Claims, 16 Drawing Sheets

(51) Int. Cl.
*G01R 31/14* (2006.01)
*G01N 29/24* (2006.01)
*G01N 29/32* (2006.01)
*G01N 29/44* (2006.01)
*G01N 29/50* (2006.01)
*G01N 29/46* (2006.01)

(52) U.S. Cl.
CPC ......... *G01N 29/4463* (2013.01); *G01N 29/46* (2013.01); *G01N 29/50* (2013.01); *G01R 31/1218* (2013.01); *G01R 31/1272* (2013.01); *G01R 31/14* (2013.01)

(58) Field of Classification Search
CPC .... G01N 29/4463; G01N 29/50; G01N 29/32; H04L 25/08
See application file for complete search history.

(56) References Cited

FOREIGN PATENT DOCUMENTS

| KR | 10-2005-0030255 A | 3/2005 |
|---|---|---|
| KR | 10-2010-0007445 A | 1/2010 |
| KR | 10-2010-0036667 A | 4/2010 |
| KR | 10-2010-0040204 A | 4/2010 |

OTHER PUBLICATIONS

International Search Report, w/ English translation thereof, issued in International Application No. PCT/KR2012/007891 dated Feb. 25, 2013.

Korean Office Action, w/ English translation thereof, issued in Korean Patent Application No. KR 10-2011-0098383 dated Mar. 29, 2013.

World of Electricity, vol. 58, No. 2, pp. 16-22.

* cited by examiner

FIG. 5
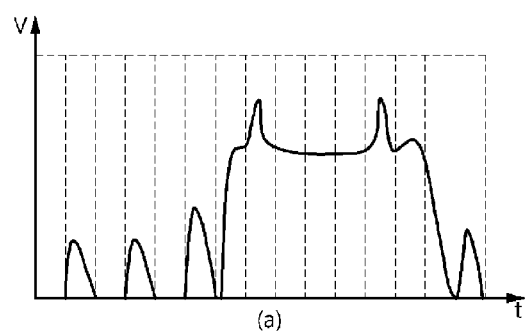
(a)
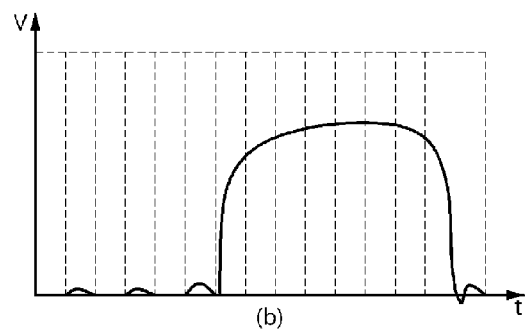
(b)

DEVICE FOR REMOVING PARTIAL DISCHARGE NOISE AND METHOD OF DIAGNOSING THE SAME

RELATED APPLICATIONS

This application is the U.S. National Phase under 35 U.S.C. §371 of International Application No. PCT/KR2012/007891, filed on Sep. 28, 2012, which in turn claims the benefit of Korean Application Nos. 10-2011-0098383, filed on Sep. 28, 2011, and 10-2011-0126368, filed on Nov. 29, 2011, the disclosures of which Applications are incorporated by reference herein.

TECHNICAL FIELD

The present invention relates to a device for removing partial discharge noise and a method of diagnosing the same, and more specifically, to a noise removing device which simultaneously detects sound waves and vibration and electromagnetic waves generated when partial discharge is generated, compares and analyzes a correlation, and thereby performs partial discharge diagnosis, and a method of diagnosing the same.

BACKGROUND ART

In general, existing methods for removing noise of partial discharge signal can be divided into two ways: Noise gating method and Offset processing method. Both methods need for installing a partial discharge sensor and an independent noise sensor. The noise gating method gets rid of a peak of a partial discharge sensor signal, which is positioned at the same time interval as a time interval at which a peak detected from the noise sensor is positioned. On the other hand, the offset processing method adjusts a base noise level by adjusting an amplification degree.

In the noise gating method, the noise sensor and the partial discharge sensor are required to be in the same condition. However, since conditions such as a phase difference, sensor sensitivity, a distance from a noise generation point, sensor directivity, and attenuation of coaxial lines are different, the method of removing a peak value has substantially low efficiency in removing noise.

In the offset processing method, since a plurality of filtering circuits overlap in a front end of an RF processing analog circuit and suppress noise, an actually generated partial discharge signal may not be detected.

Meanwhile, devices for diagnosing partial discharge in the related art include an ultrasonic microphone sensor and a detection sensor that detect a pulse voltage and ultrasound generated when partial discharge of power equipment is generated, and thereby diagnose the partial discharge.

In this case, electromagnetic waves generated when the partial discharge is generated exit through a certain exit (a gasket and/or a spacer), the electromagnetic waves are represented as a pulse waveform having an amplitude of several mV and a rise time of several ns in ground potential of a metal enclosure of the power equipment, and the partial discharge is diagnosed by detecting this pulse waveform.

In this case, when an external electromagnetic wave generation source of a 1 GHz band, for example, a mobile phone and an RF transmitter, is in a direct current (DC) end, it exerts an influence on a result value and diagnostic reliability decreases.

In addition, the devices for diagnosing partial discharge in the related art detect the partial discharge by detecting ultrasound delivered over the air when the partial discharge is generated, and a center band of a microphone for ultrasound measurement is 40 kHz.

In this case, an air passage through which the ultrasound flows out is required to be provided. However, due to characteristics of the power equipment, since a structure manufactured with an iron enclosure does not include an outflow passage of the ultrasound, it is inappropriate. In addition, when there is ambient noise in excess of 40 kHz, diagnostic conditions are inappropriate, and thereby diagnosis is impossible. When there is strong ambient electrical noise, the ultrasound sensor may operate abnormally.

DISCLOSURE

Technical Problem

The present invention provides a device and method for removing partial discharge noise. A signal detected in a partial discharge sensor is equally distributed through a distributor, electronic circuits having different operating speed characteristics are applied to a partial discharge signal and a noise signal, a difference of result values is acquired, and noise is removed using the acquired value. As a result, it is possible to remove noise of the partial discharge signal without a separate noise filter.

The present invention also provides a noise removing device (sensor) which simultaneously detects sound waves and vibration and electromagnetic waves generated when partial discharge is generated, compares a correlation, and thereby performs partial discharge diagnosis more accurately, and a device and method for diagnosing partial discharge using the noise removing device.

Technical Solution

According to an aspect of the present invention, there is provided a device for removing partial discharge noise. The device includes a partial discharge sensor configured to detect an electromagnetic wave signal generated when partial discharge is generated from a power device, a distributor configured to distribute the electromagnetic wave signal into two identical signals, a high-speed circuit unit that includes a high-speed logarithmic amplifier and performs high-speed signal processing on one signal of the two identical signals using the high-speed logarithmic amplifier, a low-speed circuit unit that includes a low-speed logarithmic amplifier and performs low-speed signal processing on the other signal of the two identical signals using the low-speed logarithmic amplifier, and a digital signal processor that measures signal strengths of a first signal output from the high-speed circuit unit and a second signal output from the low-speed circuit unit and removes a noise signal included in the electromagnetic wave signal based on a difference between a peak value of the signal strength of the first signal and a peak value of the signal strength of the second signal.

The high-speed circuit unit may detect an electromagnetic wave signal having high and low operating speeds.

The high-speed circuit unit may measure a signal strength of the detected electromagnetic wave signal and output a voltage signal proportional to the measured signal strength.

The low-speed circuit unit may detect an electromagnetic wave signal having a low operating speed.

The low-speed circuit unit may measure a signal strength of the detected electromagnetic wave signal and output a voltage signal proportional to the measured signal strength.

The high-speed logarithmic amplifier may process an input signal at a reaction rate set in the range of 6 ns to 60 ns.

The low-speed logarithmic amplifier may process an input signal at a reaction rate set in the range of 60 ns to 1000 ns.

The high-speed logarithmic amplifier and the low-speed logarithmic amplifier may have different reaction rates, and the high-speed logarithmic amplifier may have a faster reaction rate than the low-speed logarithmic amplifier.

The digital signal processor may subtract a peak value of a signal strength of an output signal of the low-speed logarithmic amplifier from a peak value of a signal strength of an output signal of the high-speed logarithmic amplifier, and remove a noise signal included in the electromagnetic wave signal.

According to another aspect of the present invention, there is provided a method of removing partial discharge noise. The method includes detecting an electromagnetic wave signal generated when partial discharge is generated from a power device, distributing, by a distributor, the electromagnetic wave signal into two identical signals, performing high-speed signal processing on one signal using a high-speed logarithmic amplifier and performing low-speed signal processing on the other signal using a low-speed logarithmic amplifier between the two signals distributed in the distributing, measuring signal strengths of an output signal of the high-speed logarithmic amplifier and an output signal of the low-speed logarithmic amplifier, and removing a noise signal included in the electromagnetic wave signal based on a difference between a peak value of a signal strength of an output signal of the high-speed logarithmic amplifier and a peak value of a signal strength of an output signal of the low-speed logarithmic amplifier.

The performing of the signal processing may include detecting, by the high-speed logarithmic amplifier, an electromagnetic wave signal having high and low operating speeds among input signals and outputting a voltage signal proportional to the detected signal strength.

Before the measuring of the signal strength, the voltage signal output from the high-speed logarithmic amplifier may be converted into a proportional electromagnetic wave signal.

The performing of the signal processing may include detecting, by the low-speed logarithmic amplifier, an electromagnetic wave signal having a low operating speed among input signals and outputting a voltage signal proportional to the detected signal strength.

Before the measuring of the signal strength, the voltage signal output from the low-speed logarithmic amplifier may be converted into a proportional electromagnetic wave signal.

In the removing of the noise signal, a peak value of a signal strength of an output signal of the low-speed logarithmic amplifier may be subtracted from a peak value of a signal strength of an output signal of the high-speed logarithmic amplifier.

According to still another aspect of the present invention, there is provided a noise removing device. The device includes an antenna configured to receive a partial discharge signal generated when partial discharge of a power device is generated, a signal amplification unit configured to adjust the partial discharge signal at a predetermined level, a distributor configured to equally distribute the partial discharge signal having a level adjusted by the signal amplification unit into three signals, a distributed digital signal processor configured to perform distributed signal processing on each signal distributed by the distributor at a high-speed, a medium-speed, and a low-speed, a differential digital signal processor configured to calculate a difference value of results of distributed signal processing for each speed of the distributed digital signal processor and remove noise included in the partial discharge signal, a device connecting unit that receives a control signal for removing noise of the partial discharge signal using a first communication method and outputs the partial discharge signal in which noise is removed to a connected external device using a second communication method, and a processor unit that controls the signal amplification unit and the distributed digital signal processor and processes a result value of the differential digital signal processor and a signal input and output through the device connecting unit.

The first communication method may include one of CAN, LIN, RS-485, and RS-422.

The second communication method may include one of optical Ethernet, Sonet/SDH, and T1/E1.

The distributed digital signal processor may include a fixed-speed type high-speed logarithmic amplifier, a variable-speed type medium-speed logarithmic amplifier, and a variable-speed type low-speed logarithmic amplifier.

The differential digital signal processor may remove noise of the partial discharge signal based on a difference value of output signals due to a reaction rate difference of the high-speed logarithmic amplifier and the low-speed logarithmic amplifier.

The differential digital signal processor may remove noise of the partial discharge signal using a subtractor.

When a signal similar to the partial discharge signal is repeated at the same time zone, the differential digital signal processor may remove noise of the partial discharge signal based on a difference value of output signals due to a reaction rate difference of the high-speed logarithmic amplifier and the variable medium-speed logarithmic amplifier.

According to yet another aspect of the present invention, there is provided a device for diagnosing partial discharge. The device includes, a noise removing device configured to remove noise of a partial discharge signal using a reaction rate difference of signals when the partial discharge signal is generated, and output a signal in which noise is removed, a laser module configured to output a laser beam to a surface of a power device when the partial discharge signal is generated and extract sound wave and vibration data from a reflection signal of the laser beam, a correlation analyzing unit configured to compare the partial discharge signal in which noise is removed input through the sensor connecting unit and the sound wave and vibration data extracted through the laser module, and analyze a correlation, and a partial discharge diagnostic unit configured to perform partial discharge diagnosis on a signal that matches the partial discharge signal in which noise is removed with at least one of a generation cycle, a time, and a phase of the sound wave and vibration data based on a result of correlation analysis of the correlation analyzing unit.

The correlation analyzing unit may extract a data change in size with respect to time from the sound wave and vibration data and extract a signal associated with 60 Hz by performing fast Fourier transform (FFT) analysis on the sound wave and vibration data.

The correlation analyzing unit may calculates data of a size component corresponding to each phase of the partial discharge signal in which a low rate noise component is removed through the noise removing device for each speed.

The correlation analyzing unit may analyze a correlation by comparing a vibration frequency of the sound wave and vibration data with at least one of a generation cycle, a time, and a phase of the partial discharge signal in which noise is removed.

The correlation analyzing unit may compare a correlation of the sound wave and vibration data generated at the same time and the partial discharge signal in which noise is removed.

The partial discharge diagnostic unit may calculate a weight based on the correlation of the sound wave and vibration data and the partial discharge signal in which noise is removed.

According to yet another aspect of the present invention, there is provided a method of diagnosing partial discharge. The method includes removing noise of a partial discharge signal using a reaction rate difference of signals through a noise removing device when the partial discharge signal is generated and outputting a signal in which noise is removed, outputting a laser beam to a surface of a power device through a laser module when the partial discharge signal is generated, and extracting sound wave and vibration data from a reflection signal of the laser beam, comparing the partial discharge signal in which noise is removed received from the noise removing device and the sound wave and vibration data extracted through the laser module, and analyzing a correlation, and performing partial discharge diagnosis on a signal that matches the partial discharge signal in which noise is removed with at least one of a generation cycle, a time, and a phase of the sound wave and vibration data and based on a result of correlation analysis of the analyzing of the correlation.

The analyzing of the correlation may include extracting a data change in size with respect to time from the sound wave and vibration data and extracting a signal corresponding to a set frequency by performing FFT analysis on the sound wave and vibration data.

The analyzing of the correlation may include calculating data of a size component corresponding to each phase of the partial discharge signal in which noise is removed through the noise removing device for each speed.

The analyzing of the correlation may include comparing a vibration frequency of the sound wave and vibration data with at least one of a generation cycle, a time, and a phase of the partial discharge signal in which noise is removed.

The analyzing of the correlation may include comparing a correlation of the sound wave and vibration data generated at the same time and the partial discharge signal in which noise is removed.

The performing of the partial discharge diagnosis may include calculating a weight based on the correlation of the sound wave and vibration data and the partial discharge signal in which noise is removed.

In the partial discharge signal in which noise is removed, the noise of the partial discharge signal may be removed based on a difference value of output signals due to a reaction rate difference of a high-speed logarithmic amplifier, a variable medium-speed logarithmic amplifier, and a variable low-speed logarithmic amplifier of the noise removing device.

Advantageous Effects

According to the present invention, the signal detected in the partial discharge sensor is equally distributed through the distributor, electronic circuits having different operating speed characteristics are applied to the partial discharge signal and the noise signal, a difference of result values is acquired, and noise is removed using the acquired value. As a result, it is possible to acquire the partial discharge signal without a separate noise filter.

According to the present invention, it is possible to remove noise of the partial discharge signal without a blind frequency band of the partial discharge. This increases efficiency.

In addition, according to the present invention, the sound wave and vibration data using the laser module and the partial discharge signal (electromagnetic waves) in which noise is removed using the active sensor are compared to each other, and the partial discharge is diagnosed by detecting a signal having a correlation. Accordingly, it is possible to improve errors of an existing single sensor method or ultrasound method, and increase accuracy when the partial discharge is detected and a location at which the partial discharge is generated is detected.

Moreover, in the present invention, excellent directivity of a laser beam is used to measure at a predetermined distance or more. Therefore, a separation distance between the main body of the power device and the sensor is secured, which allows equipment at a place that is impossible to access or difficult to access to be inspected.

Furthermore, in the present invention, noise is removed in real time using the subtractor and the like so that it is possible to implement an economic noise removing device (sensor) having a simple structure.

DESCRIPTION OF DRAWINGS

FIG. 5 shows diagrams illustrating exemplary signals output from the high-speed circuit unit and the low-speed circuit unit of the device for removing partial discharge noise according to the present invention.

MODES OF THE INVENTION

Hereinafter, embodiments of the present invention will be described with reference to the accompanying drawings.

Unlike other signals, a partial discharge signal has very rapid rise and fall times of several ns and has a very short duration. Using such characteristics of the partial discharge signal, the present invention provides a device and method for removing partial discharge noise using a speed difference.

In addition, a kind of energy generated when the partial discharge is generated includes electromagnetic waves, sound waves, light, heat, and the like. In this case, a device for diagnosing partial discharge according to the present invention simultaneously detects electromagnetic waves, sound waves, and vibration among energy generated when the partial discharge is generated, compares and analyzes a correlation, and thereby performs partial discharge diagnosis more precisely.

Also, in the present invention, as a method of diagnosing partial discharge, a speed related partial discharge analysis (SRPDA) method in which noise is removed based on a reaction rate difference of signals and thereby pure partial discharge is diagnosed is applied. Detailed technological description thereof will be provided as follows.

Figure 1:
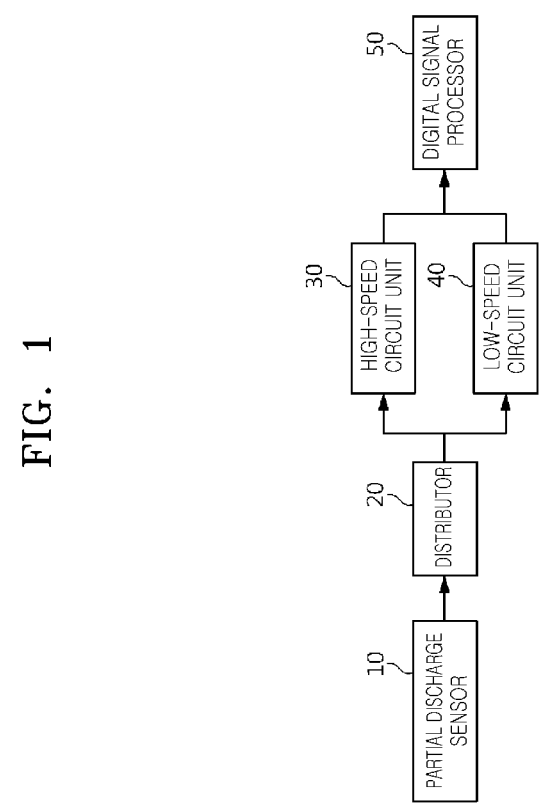
FIG. 1 is a block diagram referred to in description of a configuration of a device for removing partial discharge noise according to the present invention.

FIG. 1 is a block diagram referred to in description of a configuration of a device for removing partial discharge noise according to the present invention.

As illustrated in FIG. 1, the device for removing partial discharge noise according to the present invention includes a partial discharge sensor 10, a distributor 20, a high-speed circuit unit 30, a low-speed circuit unit 40, and a digital signal processor 50.

The partial discharge sensor 10 measures electromagnetic waves, ultrasound, and the like, generated due to partial discharge in real time. In the embodiment of the present invention, a sensor for measuring the electromagnetic waves is exemplified, but the invention is not limited thereto. It is also possible to apply different types of sensors such as an impedance sensor and an ultrasound sensor.

The distributor 20 distributes an electromagnetic wave signal input in real time through the partial discharge sensor 10 into two paths and outputs distributed signals to the high-speed circuit unit 30 and the low-speed circuit unit 40. In this case, the signals output to the high-speed circuit unit 30 and the low-speed circuit unit 40 are signals at the same time and having the same condition.

The embodiment of the present invention exemplifies a case in which the distributor 20 distributes an input partial discharge signal into two paths. However, it is also possible to distribute the signal into two or more paths. In this case, it is possible to perform signal analysis by applying different speeds more precisely.

Meanwhile, the embodiment of the present invention assumes that the same signal is input to the high-speed circuit unit 30 and the low-speed circuit unit 40 at the same time and having the same condition. However, when signals input to the high-speed circuit unit 30 and the low-speed circuit unit 40 are not the same due to a characteristic difference of an implemented circuit depending on embodiments, a zero point adjustment unit (not illustrated) for the input signal may be additionally provided.

Here, the zero point adjustment unit may adjust a zero point such that an electromagnetic wave signal is generated from the outside for calibration and is input to the partial discharge sensor, or an input point for a test is provided in a front end of the distributor and a high-frequency electrical signal is input from the outside.

Moreover, in order to prevent occurrence of a characteristic change between the high-speed circuit unit 30 and the low-speed circuit unit 40, a correction unit (not illustrated) for correcting deviation of the high-speed circuit unit 30 and the low-speed circuit unit 40 may also be additionally provided.

Here, in order to correct a signal characteristic of the high-speed circuit unit 30 and the low-speed circuit unit 40, the correction unit may correct a characteristic value of an internal circuit or correct a result value in software.

The high-speed circuit unit 30 measures signal strengths of the signals distributed from the distributor 20. In this case, the high-speed circuit unit 30 has a reaction rate in the range of 6 ns to 60 ns. Therefore, the high-speed circuit unit 30 measures a signal strength of a signal having a reaction rate in the range of 6 ns to 60 ns among input signals.

In addition, the high-speed circuit unit 30 outputs a voltage signal proportional to the measured signal strength (dBm). Here, the voltage signal output from the high-speed circuit unit 30 is referred to as a first voltage signal for convenience.

The low-speed circuit unit 40 measures signals strength of the signals distributed from the distributor 20. In this case, the low-speed circuit unit 40 has a reaction rate in the range of 60 ns to 1000 ns or more. Therefore, the low-speed circuit unit 40 measures a signal strength of a signal having a reaction rate in the range of 60 ns to 1000 ns or more among input signals.

In addition, the low-speed circuit unit 40 outputs a voltage signal proportional to the measured signal strength (dBm). Here, the voltage signal output from the low-speed circuit unit 40 is referred to as a second voltage signal for convenience.

The low-speed circuit unit 40 is able to vary the reaction rate by an external logic. In this case, a measurement time zone is minimally set, diagnosis is densely performed, and thereby the number of times a partial discharge pulse occurs and a repetition rate are obtained. When the number of times a partial discharge pulse occurs and the repetition rate are more than preset thresholds, the rate is varied. Then, the number of times a partial discharge pulse occurs and a repetition rate according to the varied rate are obtained so that precise signal analysis is performed.

When the first voltage signal and the second voltage signal are input, the digital signal processor 50 measures a voltage strength of the first voltage signal and outputs a first electromagnetic wave signal (dBm) proportional to the voltage strength of the first voltage signal. In addition, the digital signal processor 50 measures a voltage strength of the second voltage signal and outputs a second electromagnetic wave signal (dBm) proportional to the voltage strength of the second voltage signal.

In this case, the digital signal processor 50 compares peak values of the first electromagnetic wave signal and the second electromagnetic wave signal, subtracts the peak value of the second electromagnetic wave signal from the peak value of the first electromagnetic wave signal, and thereby removes noise of the signals input through the partial discharge sensor 10.

When the device for removing partial discharge noise according to the present invention is used, real time difference value data for each speed may be DAC converted, provided to the outside, and analyzed using an oscilloscope, or may be provided as an input of an existing PRPD or PRPS system.

In addition, digital data is sent to a device capable of graphic processing such as a PC and a waveform associated with the rate is output such that an operator is able to perform visual analysis.

Figure 2:
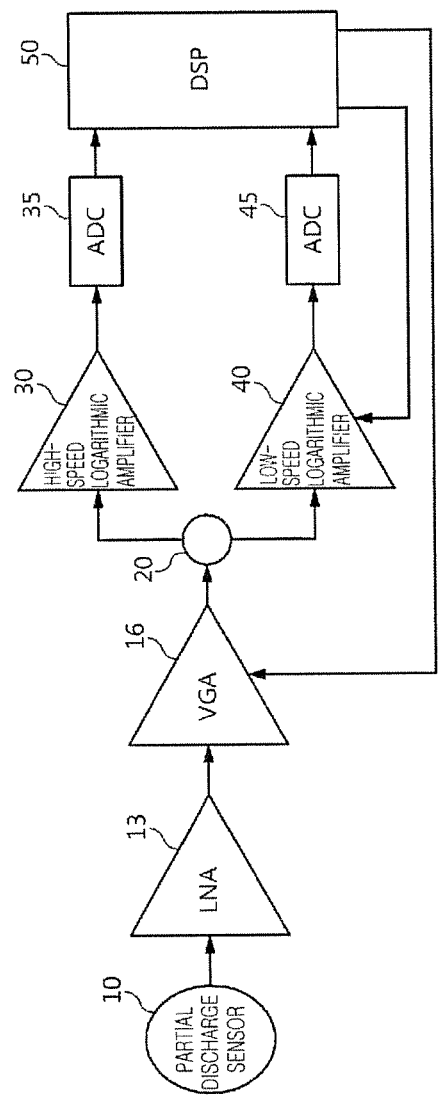
FIG. 2 is a structural diagram referred to in description of operations of the device for removing partial discharge noise according to the present invention.

FIG. 2 is a structural diagram referred to in description of operations of the device for removing partial discharge noise according to the present invention.

As illustrated in FIG. 2, a signal detected by the partial discharge sensor 10 is input to the distributor 20 through a low noise amplifier (LNA) 13 and a variable gain amplifier (VGA) 16.

The distributor 20 distributes the input signal into two paths and allows the same signal to be input to a high-speed logarithmic amplifier of the high-speed circuit unit 30 and a low-speed logarithmic amplifier of the low-speed circuit unit 40.

Since the high-speed logarithmic amplifier has a high reaction rate, it detects signals having high and low operating speeds and outputs the first voltage signal proportional to the signal strength to an analog-digital converter (ADC) 35. In this case, the ADC 35 converts the analog first voltage signal into a digital signal and outputs the converted signal to the digital signal processor (DSP) 50.

Since the low-speed logarithmic amplifier has a low reaction rate, it is unable to detect a signal having a high operating speed and is able to detect only a signal having a low operating speed. The low-speed logarithmic amplifier outputs the second voltage signal proportional to the detected signal strength to an analog-digital converter (ADC) 45. In this case, the ADC 45 converts the analog second voltage signal to a digital signal and outputs the converted signal to the digital signal processor (DSP) 50.

Here, the high-speed logarithmic amplifier and the low-speed logarithmic amplifier simultaneously process the input signals and operate at the same reference voltage and sampling frequency. In addition, the low-speed logarithmic amplifier is able to vary the speed and is able to control the speed by a control logic of the digital signal processor 50. In addition, the digital signal processor 50 controls a signal gain of the variable gain amplifier (VGA) 16.

Figure 3:
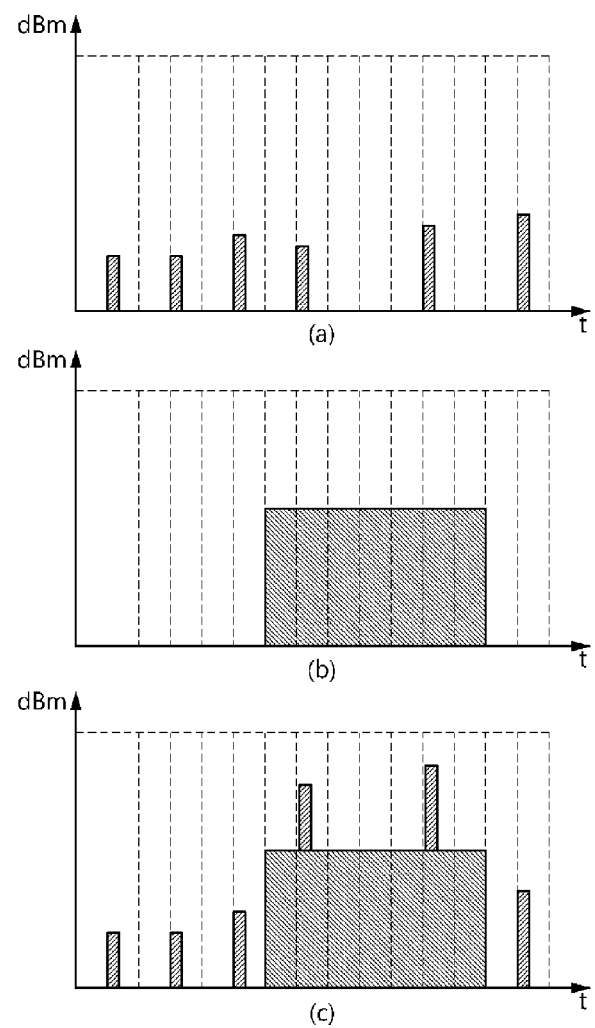
FIG. 3 shows diagrams illustrating exemplary partial discharge signals detected by the device for removing partial discharge noise according to the present invention.

FIG. 3 shows diagrams illustrating exemplary partial discharge signals detected by the device for removing partial discharge noise according to the present invention.

FIG. 3A represents a pure partial discharge signal, FIG. 3B represents a noise signal, and FIG. 3C represents a signal detected through the partial discharge sensor 10.

In other words, when partial discharge is generated from a power device, a partial discharge signal in FIG. 3A is generated. However, at the same time, a noise signal in FIG. 3B, for example, a mobile phone base station signal, may be generated.

In this case, as shown in FIG. 3C, the partial discharge sensor 10 simultaneously detects the partial discharge signal in FIG. 3A and the noise signal in FIG. 3B. Therefore, in the present invention, the pure partial discharge signal in FIG. 3A is obtained only when the noise signal is removed from the signal detected through the partial discharge sensor 10.

For this purpose, in the present invention, in order to remove noise using an operating speed difference of FIGS. 3A and 3B, the signal in FIG. 3C is processed in the high-speed circuit unit 30 and the low-speed circuit unit 40.

Figure 4:
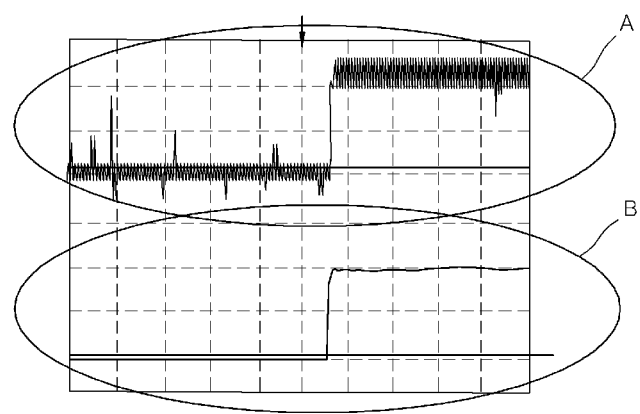
FIG. 4 is a diagram illustrating exemplary measurement data of a high-speed circuit unit and a low-speed circuit unit which are applied to the device for removing partial discharge noise according to the present invention.

FIG. 4 is a diagram illustrating exemplary measurement data of the high-speed circuit unit 30 and the low-speed circuit unit 40 which are applied to the device for removing partial discharge noise according to the present invention.

In FIG. 4, a region A represents signal measurement data of the high-speed circuit unit 30. In the embodiment of FIG. 4, the high-speed circuit unit 30 has a reaction rate of 24 ns. Meanwhile, a region B represents measurement data of the low-speed circuit unit 40 and a reaction rate is set to 1000 ns.

Here, whereas the partial discharge signal in FIG. 3A has a high operating speed, the mobile phone base station signal in FIG. 3B has a low operating speed.

Therefore, as illustrated in FIG. 4, it is observed that the high-speed partial discharge signal and the low-speed mobile phone base station signal are simultaneously detected in the region A. On the other hand, it is observed that no high-speed partial discharge signal is detected and only the low-speed mobile phone base station signal is detected in the region B.

In this way, since the low-speed circuit unit 40 has the low reaction rate, it is unable to detect the high-speed partial discharge signal. Therefore, the signal detected by the low-speed circuit unit 40 is considered as a noise signal of the partial discharge.

FIG. 5 shows diagrams illustrating exemplary signals output from the high-speed circuit unit 30 and the low-speed circuit unit 40 of the device for removing partial discharge noise according to the present invention.

FIG. 5A represents an output signal of the high-speed circuit unit 30. That is, the high-speed circuit unit 30 detects both the partial discharge signal and the mobile phone base station signal. In this case, since the high-speed circuit unit 30 outputs the first voltage signal proportional to the signal strength of the detected electromagnetic wave signal, a signal waveform in FIG. 5A is output.

Meanwhile, FIG. 5B represents an output signal of the low-speed circuit unit 40. That is, the low-speed circuit unit 40 is unable to detect both the partial discharge signal and the mobile phone base station signal, and detects only the mobile phone base station signal. In this case, since the low-speed circuit unit 40 outputs the second voltage signal proportional to the signal strength of the detected electromagnetic wave signal, a signal waveform in FIG. 5B is output.

The first voltage signal and the second voltage signal in FIGS. 5A and 5B are converted into digital signals by the ADCs 35 and 45, respectively, and are input to the digital signal processor 50.

Figure 6:
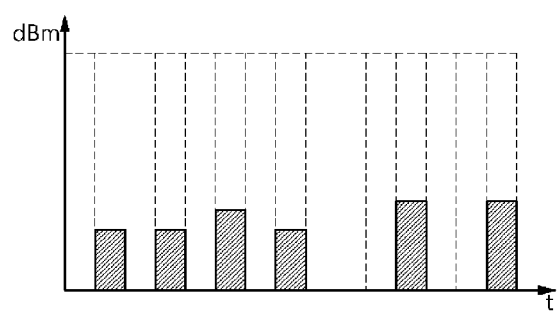
FIG. 6 is a diagram illustrating an exemplary partial discharge signal in which noise is removed by the device for removing partial discharge noise according to the present invention.

FIG. 6 is a diagram illustrating an exemplary partial discharge signal in which noise is removed by the device for removing partial discharge noise according to the present invention.

When the first voltage signal and the second voltage signal are input, the digital signal processor 50 outputs the first electromagnetic wave signal (dBm) proportional to the voltage strength of the first voltage signal. In addition, the digital signal processor 50 outputs the second electromagnetic wave signal (dBm) proportional to the voltage strength of the second voltage signal.

In this case, the digital signal processor 50 compares peak values of the first electromagnetic wave signal and the second electromagnetic wave signal and subtracts the peak value of the second electromagnetic wave signal from the peak value of the first electromagnetic wave signal. A result of subtracting the peak value of the second electromagnetic wave signal from the peak value of the first electromagnetic wave signal is shown in FIG. 6.

As a result, when FIG. 6 and FIG. 3A are compared, it is observed that the result of subtracting the peak value of the second electromagnetic wave signal from the peak value of the first electromagnetic wave signal has a shape close to the pure partial discharge signal.

Therefore, when the device for removing partial discharge noise according to the present invention is used, it is possible to detect the partial discharge signal having high reliability.

Operations of a device for removing partial discharge noise configured as above according to the present invention are as follows.

Figure 7:
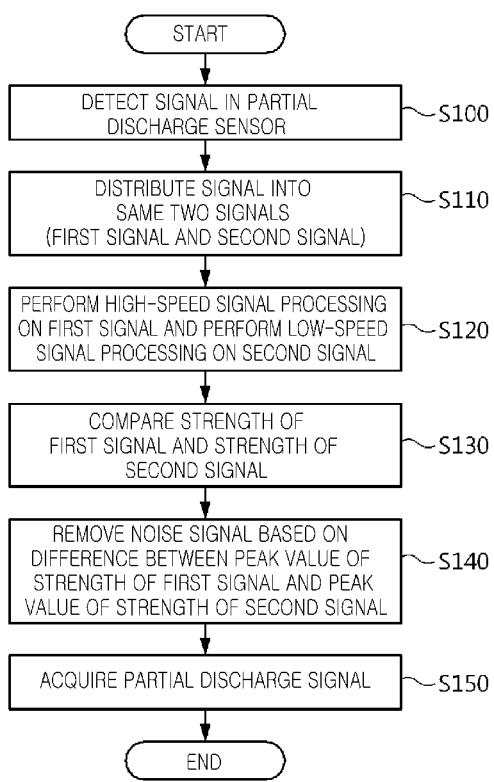
FIG. 7 is a flowchart illustrating an operation flow of a method of removing partial discharge noise according to the present invention.

FIG. 7 is a flowchart illustrating an operation flow of a method of removing partial discharge noise according to the present invention.

As illustrated in FIG. 7, when partial discharge is generated from the power device, the device for removing partial discharge noise according to the present invention detects the generated partial discharge using the partial discharge sensor 10 (S100).

In this case, in order to remove noise of the signal detected by the partial discharge sensor 10, the device for removing partial discharge noise distributes the signal detected in the operation of S100 into two identical signals through the distributor 20 (S110) and outputs the signals distributed in the operation of S110 to a high-speed logarithmic amplifier 31 and a low-speed logarithmic amplifier 41.

The high-speed logarithmic amplifier 31 and the low-speed logarithmic amplifier 41 perform high-speed and low-speed signal processing on the input signal, respectively (S120). That is, the high-speed logarithmic amplifier 31 performs the high-speed signal processing on one of the two distributed signals, and the low-speed logarithmic amplifier 41 performs the low-speed signal processing on the other of the two distributed signals.

Then, the device for removing partial discharge noise detects and compares a peak value of an output signal of the high-speed logarithmic amplifier 31 and a peak value of an output signal of the low-speed logarithmic amplifier 41 (S130), subtracts the peak value of the output signal of the low-speed logarithmic amplifier 41 from the peak value of the output signal of the high-speed logarithmic amplifier 31, and thereby removes noise of the signal detected by the partial discharge sensor 10 (S140).

Accordingly, the device for removing partial discharge noise obtains the partial discharge signal in which noise is removed (S150).

Figure 8:
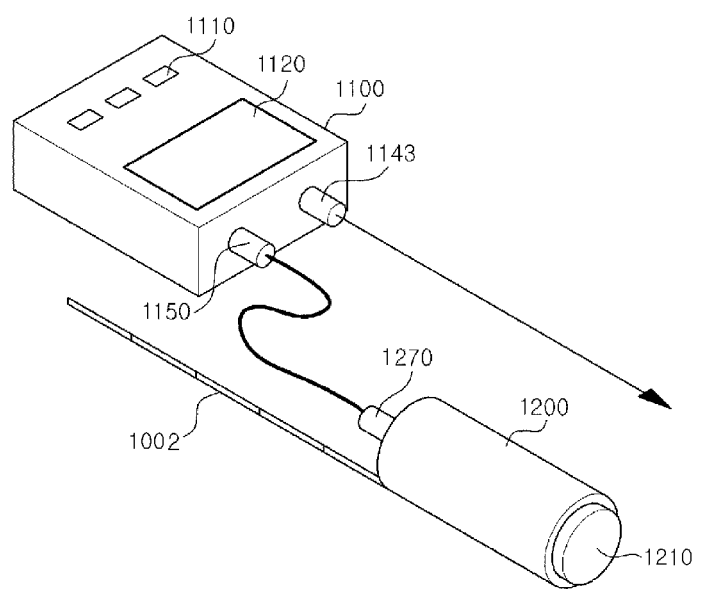
FIG. 8 is a diagram illustrating a configuration of a device for diagnosing partial discharge according to the present invention.

In addition, FIG. 8 is a diagram illustrating a configuration of a device for diagnosing partial discharge according to the present invention.

As illustrated in FIG. 8, a device for diagnosing partial discharge 1100 according to the present invention is divided into a main body of the device for diagnosing partial discharge, a noise removing device (sensor) 1200, and a laser module 1140.

In this case, it is preferable that the noise removing device (sensor) 1200 be provided outside the main body of the device for diagnosing partial discharge and the laser module 1140 be integrally provided with the main body of the device for diagnosing partial discharge in an internal or external surface of the main body of the device for diagnosing partial discharge.

However, a laser transmitting and receiving unit of the laser module 1140 is disposed outside the main body of the device for diagnosing partial discharge. In addition, the noise removing device 1200 is fixed through a support and is disposed in a location which a person is unable to access, but the invention is not limited thereto.

The laser module 1140 outputs a laser beam to a surface of the power device to be diagnosed through the laser transmitting and receiving unit. At this time, the output laser beam is received through the laser transmitting and receiving unit as a reflection beam in a state of having a sound wave component. The laser transmitting and receiving unit may be formed by separating a laser transmitting unit 1143 and a laser receiving unit or by integrating them.

In this case, the laser module 1140 amplifies a frequency included in the received reflection beam, acquires a vibration frequency, and then outputs the result to a control unit (not illustrated) of the device for diagnosing partial discharge 1100.

The noise removing device (sensor) 1200 is assumed to be an active sensor, but the invention is not limited thereto.

The noise removing device 1200 applies a noise reduction method according to a reaction rate difference, removes noise of the detected partial discharge signal under control of the control unit of the device for diagnosing partial discharge 1100, and then outputs the partial discharge signal in which noise is removed to the control unit of the device for diagnosing partial discharge 1100.

In this case, the main body of the device for diagnosing partial discharge 1100 and the noise removing device 1200 are connected using a photoelectric composite medium method that uses an optical Ethernet method and a CAN method as a communication protocol. Specifically, a control signal serving as a downstream signal and power use a communication protocol of the CAN method and a copper wire as a communication medium. Meanwhile, an upstream response signal uses a communication protocol of the optical Ethernet method and a plastic optical fiber (POF) as a communication medium. For example, an optical fiber, a glass optical fiber, and the like may be used.

Here, the control signal has the following characteristics.
An external signal synchronized at 60 Hz
A control signal of a variable medium-speed logarithmic amplifier and a variable low-speed logarithmic amplifier
A control signal of a variable gain amplifier (VGA)
Meanwhile, the response signal has the following characteristics.
A digital conversion signal having a waveform synchronized at 60 Hz of a time division variable medium-speed logarithmic amplifier and variable low-speed logarithmic amplifier in which noise is removed.
A simple diagnosis result (alarm output): provide a self-diagnosis result using a high-speed computing algorithm embedded in the digital signal processor (DSP).

Figure 9:
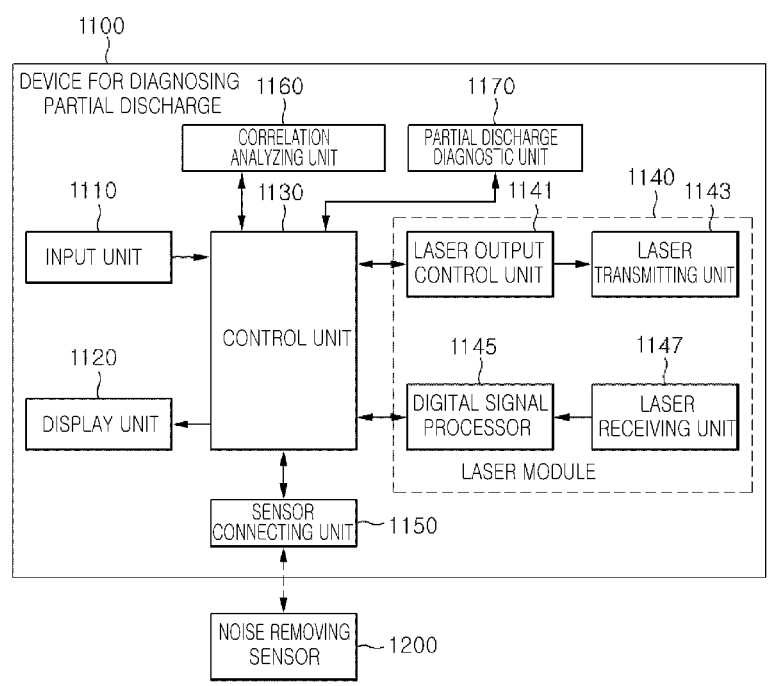
FIG. 9 is a block diagram referred to in description of a configuration of the device for diagnosing partial discharge according to the present invention.

FIG. 9 is a block diagram referred to in description of a configuration of the device for diagnosing partial discharge according to the present invention.

As illustrated in FIG. 9, the device for diagnosing partial discharge 1100 according to the present invention includes an input unit 1110, a display unit 1120, a control unit 1130, the laser module 1140, a sensor connecting unit 1150, the noise removing device 1200, a correlation analyzing unit 1160, and a partial discharge diagnostic unit 1170. In this case, the control unit 1130 controls operations of each unit of the device for diagnosing partial discharge 1100.

The input unit 1110 may be provided in the form of a key button outside the device for diagnosing partial discharge 1100 or provided in the form of a soft key implemented on a touch screen. In this case, the input unit 1110 outputs a corresponding signal according to key manipulation to the control unit 1130.

The display unit 1120 may be provided in the form of a monitor or a touch screen outside the device for diagnosing partial discharge 1100. In this case, the display unit 1120 outputs an operation state and result of the device for diagnosing partial discharge 1100.

The laser module 1140 includes a laser output control unit 1141, the laser transmitting unit 1143, a digital signal processor 1145, and a laser receiving unit 1147. Here, the laser transmitting unit 1143 and the laser receiving unit 1147 may be provided separately or integrally.

The laser output control unit 1141 transmits a laser output signal to the laser transmitting unit 1143 according to the control signal from the control unit 1130.

The laser transmitting unit 1143 includes a laser beam output unit therein, drives the laser beam output unit according to the laser output signal from the laser output control unit 1141, and outputs a laser beam to a surface of the power device of which partial discharge is to be diagnosed.

The laser receiving unit 1147 receives a beam type reflection signal of the laser beam output from the laser transmitting unit 1143 from the surface of the power device. In this case, the received reflection beam includes a sound wave and vibration component due to vibration generated at the surface of the power device.

The digital signal processor 1145 processes the reflection signal received by the laser receiving unit 1147. Specifically, the digital signal processor 1145 amplifies the reflection signal received by the laser receiving unit 1147, extracts sound wave and vibration data, and outputs the extracted sound wave and vibration data to the control unit 1130. Here, the sound wave and vibration data includes vibration frequency information of the reflection signal.

Since the noise removing device 1200 is provided separately outside the main body of the device for diagnosing partial discharge, it is connected to the main body of the device for diagnosing partial discharge 1100 through the sensor connecting unit 1150.

The noise removing device 1200 removes noise of the partial discharge signal based on a difference value of output signals due to a reaction rate difference of a high-speed logarithmic amplifier 1233, a variable medium-speed logarithmic amplifier 1235, and a variable low-speed logarithmic amplifier 1237. That is, since sums of a rise time, a duration, and a fall time of the partial discharge signal and the noise signal are different, noise is removed from the partial discharge signal using the difference. In this case, the partial discharge signal in which noise is removed is output to the control unit 1130 through the sensor connecting unit 1150.

A detailed configuration of the noise removing device 1200 will be described with reference to embodiments of FIGS. 10 and 11.

The correlation analyzing unit 1160 compares the partial discharge signal in which noise is removed output from the noise removing device 1200 and the sound wave and vibration data extracted through the laser module 1140, and analyzes a correlation of each signal.

In this case, the correlation analyzing unit 1160 extracts a data change in size with respect to time from the sound wave and vibration data, performs fast Fourier transform (FFT) analysis on the sound wave and vibration data, and extracts a signal associated with a commercial power frequency (60 Hz).

In addition, the correlation analyzing unit 1160 calculates data of a size component corresponding to each phase of the partial discharge signal in which noise is removed through the noise removing device 1200 for each reaction rate.

The correlation analyzing unit 1160 compares the partial discharge signal in which noise is removed that is generated at the same time as at least one of a generation cycle, a time, and a phase of the sound wave and vibration data, a time, and a phase, and analyzes a correlation.

Based on a result of correlation analysis of the correlation analyzing unit 1160, the partial discharge diagnostic unit 1170 performs partial discharge diagnosis on a signal that matches the partial discharge signal in which noise is removed with at least one of a generation cycle, a time, and a phase of the sound wave and vibration data.

In this case, the partial discharge diagnostic unit 1170 calculates a weight according to the correlation of the sound wave and vibration data and the partial discharge signal in which noise is removed, and performs partial discharge diagnosis by applying the weight.

Figure 10:
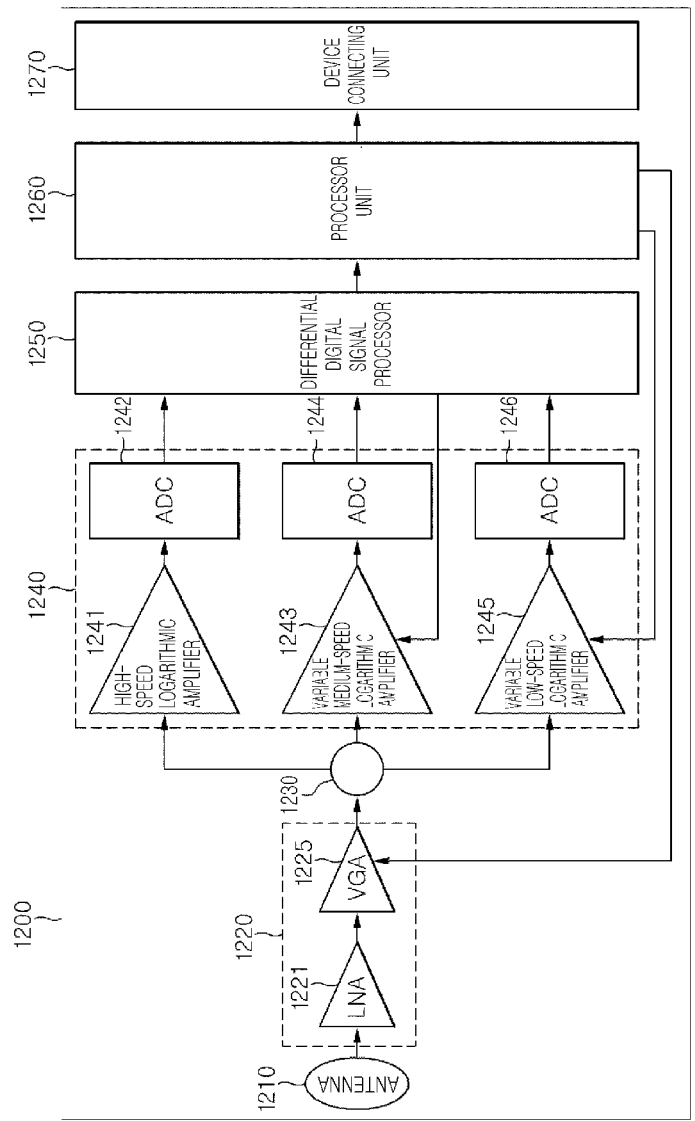
FIG. 10 is a block diagram referred to in description of a configuration of a noise removing device according to the present invention.

FIG. 10 is a block diagram referred to in description of a configuration of the noise removing device according to the present invention.

The most important technology for diagnosing partial discharge using the electromagnetic waves is denoising technology capable of distinguishing ambient noise from a partial discharge signal in a received electromagnetic wave signal. In this case, most noise is wireless electromagnetic waves for electronic communication or power noise such as a corona signal generated from an ambient power device.

Unlike other signals, the partial discharge signal has a very rapid and short rise time, duration, and fall time of several ns. Therefore, the noise removing device 1200 according to the present invention applies a method of removing noise from an initially generated partial discharge signal using a response characteristic difference of the partial discharge signal and the noise signal.

As illustrated in FIG. 10, the noise removing device 1200 according to the present invention includes an antenna (a partial discharge sensor) 1210, a signal amplification unit 1220, a distributor 1230, a distributed digital signal processor 1240, a differential digital signal processor 1250, a processor unit 1260, and a device connecting unit 1270.

When partial discharge of the power device is generated, the antenna (partial discharge sensor) 1210 receives the generated partial discharge signal.

That is, when the partial discharge signal is generated from the power device, the generated partial discharge signal is input to the noise removing device 1200 through the antenna 1210. In this case, the partial discharge signal input through the antenna 1210 is a signal in which the noise signal is mixed. As an example, the antenna 1210 may be implemented in the form of a chip antenna, and a passive sensor may be used.

The signal amplification unit 1220 includes a low noise amplifier (hereinafter referred to as an "LNA") 1221 and a variable gain amplifier (hereinafter referred to as a "VGA") 1225. In this case, the signal amplification unit 1220 adjusts the partial discharge signal at a predetermined level using the LNA 1221 and the VGA 1225.

The distributor 1230 equally distributes the partial discharge signal having a level adjusted by the signal amplification unit 1220 into two or more signals. FIG. 10 exemplifies a case in which a signal is equally distributed into three signals. The three signals equally distributed by the distributor 1230 are input to the distributed digital signal processor 1240.

The distributed digital signal processor 1240 performs distributed signal processing on each signal distributed by the distributor 1230 at a high-speed, a medium-speed, and a low-speed.

Here, the distributed digital signal processor 1240 includes a fixed-speed type high-speed logarithmic amplifier 1241, a variable-speed type medium-speed logarithmic amplifier 1243, a variable-speed type low-speed logarithmic amplifier 1245, and analog-digital converters (hereinafter referred to as "ADCs") 1242, 1244, and 1246 which convert an output signal of each logarithmic amplifier from an analog signal into a digital signal.

Accordingly, each signal distributed by the distributor 1230 is input to the high-speed logarithmic amplifier 1241, the variable medium-speed logarithmic amplifier 1243, and the variable low-speed logarithmic amplifier 1245. In this case, the signals input to the high-speed logarithmic amplifier 1241, the variable medium-speed logarithmic amplifier 1243, and the variable low-speed logarithmic amplifier 1245 are signals 40 at the same time and having the same condition.

Meanwhile, in the embodiment of the present invention, it is assumed that the same signal at the same time and having the same condition is input to the high-speed logarithmic amplifier 1241, the variable medium-speed logarithmic amplifier 1243, and the variable low-speed logarithmic amplifier 1245. However, when signals input to the high-speed logarithmic amplifier 1241, the variable medium-speed logarithmic amplifier 1243, and the variable low-speed logarithmic amplifier 1245 are not the same due to a characteristic difference of an implemented circuit depending on embodiments, a zero point adjustment unit (not illustrated) for the input signal may be additionally provided.

Here, the zero point adjustment unit may adjust a zero point such that an electromagnetic wave signal is generated from the outside for calibration and is input to the partial discharge sensor, or an input point for a test is provided in a front end of the distributor 1230 and a high-frequency electrical signal is input from the outside.

Moreover, in order to prevent occurrence of a characteristic change among the high-speed logarithmic amplifier 1241, the variable medium-speed logarithmic amplifier 1243, and the variable low-speed logarithmic amplifier 1245, a correction unit (not illustrated) for correcting deviation of the high-speed logarithmic amplifier 1241, the variable medium-speed logarithmic amplifier 1243, and the low-speed logarithmic amplifier 1245 may also be additionally provided.

Here, in order to correct a signal characteristic of the high-speed logarithmic amplifier 1241, the variable medium-speed logarithmic amplifier 1243, and the variable low-speed logarithmic amplifier 1245, the correction unit may correct a characteristic value of an internal circuit or correct a result value in software.

Meanwhile, since the high-speed logarithmic amplifier 1241 of the distributed digital signal processor 1240 has a high reaction rate, it detects signals having high, medium, and low operating speeds and outputs the first voltage signal proportional to the signal strength to the ADC 1242.

In this case, the ADC 1242 converts the analog first voltage signal into a digital signal and outputs the converted signal to the differential digital signal processor 1250.

Since the variable medium-speed logarithmic amplifier 1243 has a medium reaction rate, it is unable to detect a signal having a high operating speed, that is, the partial discharge signal, but is able to detect signals having a medium and low operating speed, and outputs the second voltage signal proportional to the signal strength to the ADC 1244.

In this case, the ADC 1244 converts the analog second voltage signal into a digital signal and outputs the converted signal to the differential digital signal processor 1250.

Since the variable low-speed logarithmic amplifier 1245 has a low reaction rate, it is unable to detect a signal having a high and medium operating speed and is able to detect only a signal having a low operating speed. The low-speed logarithmic amplifier 1245 outputs a third voltage signal proportional to the detected signal strength to the ADC 1246.

In this case, the ADC 1246 converts the analog third voltage signal into a digital signal and outputs the converted signal to the differential digital signal processor 1250.

Here, the high-speed logarithmic amplifier 1241, the variable medium-speed logarithmic amplifier 1243, and the variable low-speed logarithmic amplifier 1245 simultaneously process the input signals and operate at the same reference voltage and sampling frequency.

In addition, the variable medium-speed logarithmic amplifier 1243 is able to vary the speed and is able to control the speed by a control logic of the processor unit 1260. Speed variation of the variable medium-speed logarithmic amplifier 1243 may be passively controlled by a control signal input from the outside in some cases.

The differential digital signal processor 1250 calculates a difference value of distributed signal processing results for each speed of the distributed digital signal processor 1240 and removes noise included in partial discharge signal.

Here, based on a difference value of output signals due to a reaction rate difference of the high-speed logarithmic amplifier and the variable low-speed logarithmic amplifier, the differential digital signal processor 1250 removes noise of the partial discharge signal.

As an embodiment, when the first voltage signal, the second voltage signal, and the third voltage signal output from the high-speed logarithmic amplifier 1241, the variable medium-speed logarithmic amplifier 1243, and the variable low-speed logarithmic amplifier 1245 are input, the differential digital signal processor 1250 measures voltage strengths of the first voltage signal, the second voltage signal, and third voltage signal and outputs a first electromagnetic wave signal (dBm), a second electromagnetic wave signal (dBm), and a third electromagnetic wave signal (dBm) which are proportional to the voltage strengths of the first voltage signal, the second voltage signal, and the third voltage signal, respectively.

In this case, the differential digital signal processor 1250 compares peak values of the first electromagnetic wave signal, the second electromagnetic wave signal, and the third electromagnetic wave signal, subtracts the peak value of the second electromagnetic wave signal and the third electromagnetic wave signal from the peak value of the first electromagnetic wave signal, and thereby removes noise of the input partial discharge signal.

More specifically, whereas the partial discharge signal is a high-speed signal having a time in which a sum of a rise time, a duration, and a fall time is very short, the noise signal is a low-speed signal having a time in which a sum of a rise time, a duration, and a fall time is long. Therefore, the signal passing through the high-speed logarithmic amplifier 1241 becomes the partial discharge signal+the noise signal, and the signal passing through the variable low-speed logarithmic amplifier 1245 becomes the noise signal. Accordingly, when the signal passing through the variable low-speed logarithmic amplifier 1245 is subtracted from the signal passing through the high-speed logarithmic amplifier 1241, a remaining signal becomes the partial discharge signal in which noise is removed.

Meanwhile, the differential digital signal processor 1250 may include a subtractor therein, and noise of the partial discharge signal may also be removed by subtracting the third voltage signal from the first voltage signal using the subtractor. Needless to say, when the differential digital signal processor 1250 removes noise of the partial discharge signal using the subtractor, the ADCs 1242, 1244, and 1246 of the distributed digital signal processor 1240 may not be provided.

In addition, when a signal similar to the partial discharge signal is repeated at the same time zone, the differential digital signal processor 1250 may remove noise of the partial discharge signal more precisely based on a difference value of output signals due to a reaction rate difference of the high-speed logarithmic amplifier 1241 and the variable medium-speed logarithmic amplifier 1243/the variable low-speed logarithmic amplifier 1245.

The device connecting unit 1270 is a connecting unit that connects the noise removing device (sensor) and an external device, for example, a partial discharge measurement device, and may include a connector and the like that connects the noise removing device and the external device.

The device connecting unit 1270 receives a control signal for removing noise of the partial discharge signal using a first communication method and outputs the partial discharge signal in which noise is removed to the external device using a second communication method.

A detailed configuration of the device connecting unit 1270 will be described with reference to FIG. 11.

The processor unit 1260 controls the signal amplification unit 1220 and the distributed digital signal processor 1240 and processes a result value of the differential digital signal processor 1250 and signals input or output through the device connecting unit 1270. Meanwhile, the processor unit 1260 includes an embedded system having a memory function such that an interannual variation and a history are managed and failure notification is possible.

Figure 11:
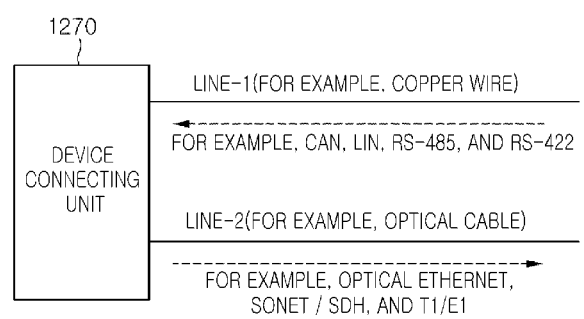
FIG. 11 is a diagram referred to in description of an exemplary configuration of a device connecting unit of FIG. 10.

FIG. 11 is a diagram referred to in description of an exemplary detailed configuration of the device connecting unit according to the present invention. As illustrated in FIG. 11, the device connecting unit 1270 is divided into a communication line to which a signal is input from the external device and a communication line to which a signal is output to the external device.

First, in the device connecting unit 1270, the communication line to which a signal is input from the external device, that is, a LINE_1, may be implemented using a copper wire and the like. In this case, the LINE_1 receives a control signal for removing noise of the partial discharge signal using the first communication method. Here, the downstream control signal applies a communication method having a small data capacity but having excellent noise tolerance. As an example, any communication method of CAN, LIN, RS-485, and RS-422 may be applied as the first communication method.

On the other hand, in the device connecting unit 1270, the communication line to which a signal is input from the external device, that is, a LINE_2, may be implemented using an optical fiber, that is, an optical cable such as a glass optical fiber and a plastic optical fiber. In this case, the LINE_2 outputs a data signal of the noise removing device, that is, the partial discharge signal in which noise is removed and the like, to the external device using the second communication method.

Here, the upstream data signal applies a communication method having a large data capacity and excellent noise tolerance. As an example, any communication method of optical Ethernet, 155 Mbps Sonet/SDH, and 1.544 Mbps/2.048 Mbps T1/E1 may be applied as the second communication method.

Therefore, the noise removing device 1200 finally outputs the partial discharge signal in which noise is removed through the optical cable connected to the main body of the device for diagnosing partial discharge.

Figure 12:
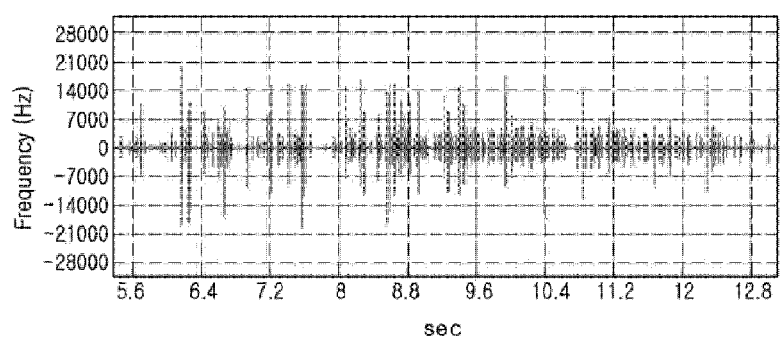
FIGS. 12 to 14 are diagrams referred to in description of exemplary operations of a device for diagnosing partial discharge according to the present invention.
Figure 13:
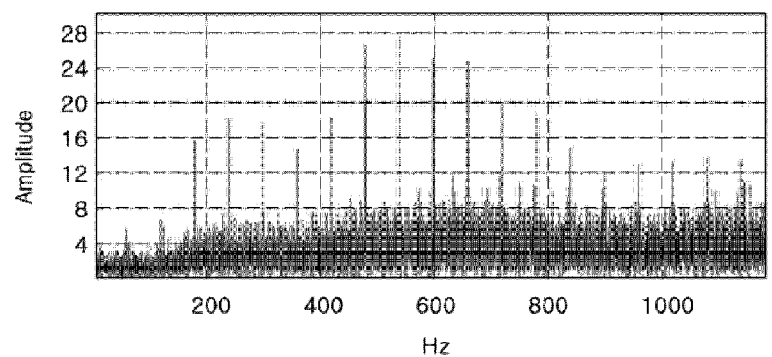
Figure 14:
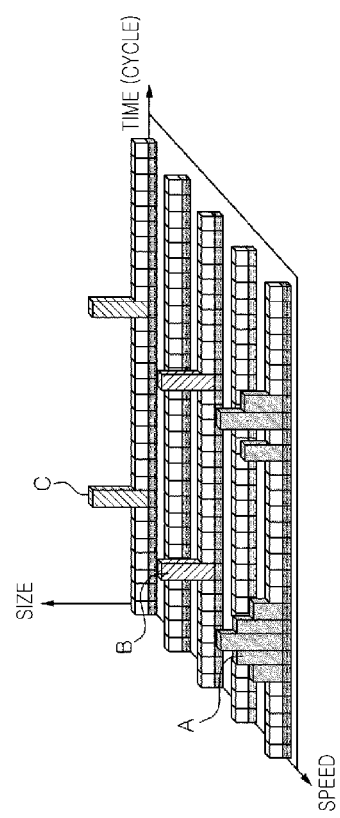

FIGS. 12 to 14 are diagrams referred to in description of exemplary operations of the device for diagnosing partial discharge according to the present invention.

First, FIG. 12 represents a data change in size with respect to time in the sound wave and vibration data acquired through the laser module. In addition, FIG. 13 represents an example in which FFT is performed on the sound wave and vibration data acquired through the laser module at a set frequency. In FIG. 13, it is observed that a frequency component of 60 Hz is detected.

Meanwhile, FIG. 14 represents data of a size component corresponding to each phase of the partial discharge signal in which noise is removed through the noise removing device 1200 for each speed.

The correlation analyzing unit 1160 compares a frequency component of 60 Hz serving as a commercial power frequency of the sound wave and vibration data with a size according to a phase of the partial discharge signal for each speed referring to graphs in FIGS. 12 to 14, and identifies a signal that matches at least one of a generation cycle, a time, and a phase. In this case, the correlation analyzing unit 1160 determines that there is a correlation between signals matching at least one of the generation cycle, the time, and the phase.

Therefore, based on an analysis result of the correlation analyzing unit 1160, the partial discharge diagnostic unit 1170 performs partial discharge diagnosis on a signal having a correlation, in other words, a signal that matches the frequency component of 60 Hz of the sound wave and vibration data with at least one of the generation cycle, the time, and the phase of a size according to a phase of the partial discharge signal for each speed.

Figure 15:
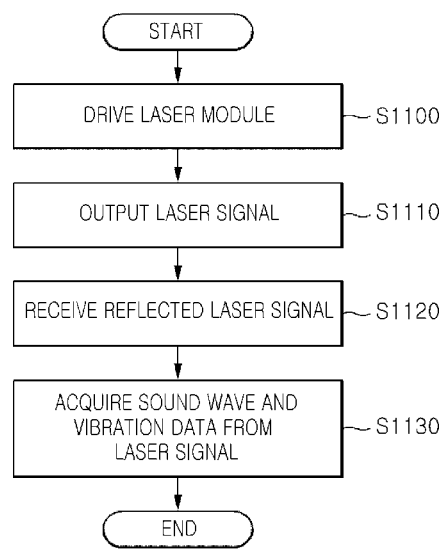
FIG. 15 is a flowchart illustrating an operation flow of a laser module of the device for diagnosing partial discharge according to the present invention.

FIG. 15 is a flowchart illustrating an operation flow of the laser module of the device for diagnosing partial discharge according to the present invention.

As illustrated in FIG. 15, when the laser module 1140 is driven by the control unit 1130 of the device for diagnosing partial discharge 1100 (S1100), the laser module 1140 outputs a laser signal to a surface of the power device to be diagnosed through the laser transmitting and receiving unit (S1110).

Then, the laser signal output in the operation of S1110 is reflected at a surface of the power device, and the laser receiving unit 1147 receives a reflection signal including a sound wave and vibration component due to vibration of the surface of the power device (S1120).

Accordingly, the digital signal processor 1145 of the laser module 1140 acquires the sound wave and vibration data from the reflection signal received in the operation of S1120 (S1130).

Figure 16:
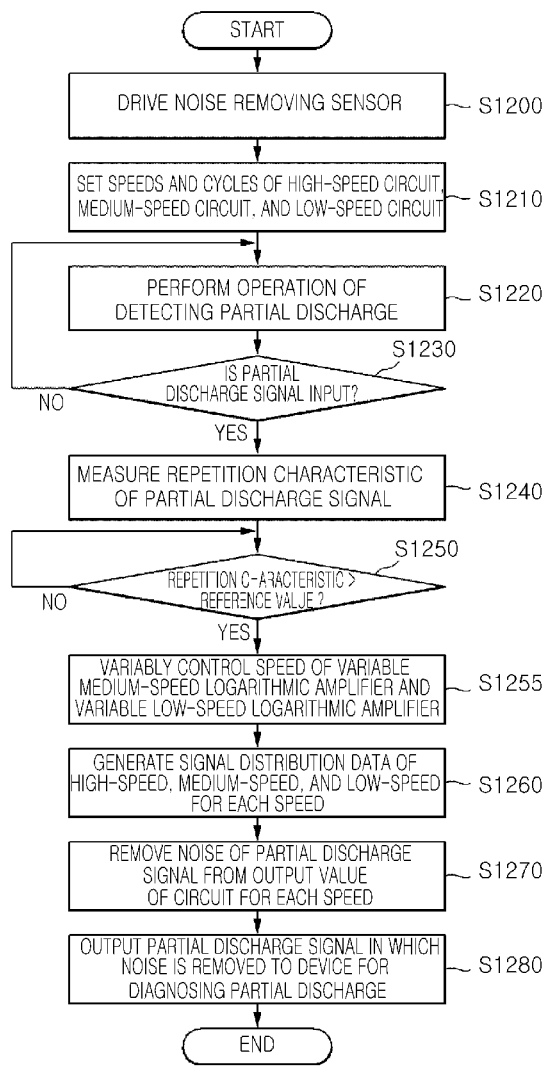
FIG. 16 is a flowchart illustrating an operation flow of the noise removing device according to the present invention.

FIG. 16 is a flowchart illustrating an operation flow of the noise removing device according to the present invention.

As illustrated in FIG. 16, when the noise removing device 1200 is driven by the control unit 1130 of the device for diagnosing partial discharge 1100 (S1200), the noise removing device 1200 sets speeds and cycles of a high-speed circuit, a medium-speed circuit, and a low-speed circuit (S1210).

In this case, the high-speed circuit has a high operating speed, the medium-speed circuit has a medium operating speed, and the low-speed circuit has a low operating speed. Since the medium-speed circuit and the low-speed circuit include a variable logarithmic amplifier, it is possible to vary the speed according to an operation of the processor unit later.

Then, the noise removing device 1200 performs an operation of detecting partial discharge (S1220) and detects the partial discharge signal when partial discharge is generated from the power device. In this case, the detected partial discharge signal is a signal having a noise component.

Therefore, when the partial discharge signal is input (S1230), the noise removing device 1200 removes noise included in the partial discharge signal from an output value of the circuit for each speed (S1270). Here, the circuit for each speed refers to the high-speed circuit, the medium-speed circuit, and the low-speed circuit.

More specifically, when the partial discharge signal is detected, the distributor 1230 distributes the partial discharge signal into three signals having the same condition. In this case, the three distributed signals are input to the high-speed logarithmic amplifier 1241 of the high-speed circuit, the variable medium-speed logarithmic amplifier 1243 of the medium-speed circuit, and the variable low-speed logarithmic amplifier 1245 of the low-speed circuit. The high-speed logarithmic amplifier 1241, the variable medium-speed logarithmic amplifier 1243, and the variable low-speed logarithmic amplifier 1245 detect and output the signal input according to the set operating speed.

In this case, a differential digital signal processor of the noise removing device 1200 compares a difference of output values of signals output from the high-speed logarithmic amplifier 1241, the variable medium-speed logarithmic amplifier 1243, and the variable low-speed logarithmic amplifier 1245, subtracts the output value of the variable low-speed logarithmic amplifier 1245 from the output value of the high-speed logarithmic amplifier 1241, and removes noise included in the partial discharge signal.

When a signal similar to the partial discharge signal is repeated at the same time zone, the differential digital signal processor of the noise removing device 1200 compares the output value of the high-speed logarithmic amplifier 1241 and the output value of the variable medium-speed logarithmic amplifier 1243, and is able to precisely remove noise of the partial discharge signal.

Additionally, when the partial discharge signal is input in the operation of S1230, the noise removing device 1200 measures a repetition characteristic of the partial discharge signal (S1240) and compares it with a reference value. The reference value may be set to a default value or may be changed in operation. When the repetition characteristic of the partial discharge signal does not exceed the reference value (S1250), the process returns to the operation after the operation of S1240, and the repetition characteristic of the partial discharge signal is compared with the reference value.

On the other hand, when the repetition characteristic of the partial discharge signal exceeds the reference value (S1250), the preset speeds of the variable medium-speed logarithmic amplifier 1243 and the variable low-speed logarithmic amplifier 1245 are varied (S1255), signal distribution data of precisely adjusted signals of the high-speed, the medium-speed, and the low-speed is generated for each speed (S1260), and noise of the partial discharge signal is removed by comparing a rate difference of each of the signals (S1270).

Figure 17:
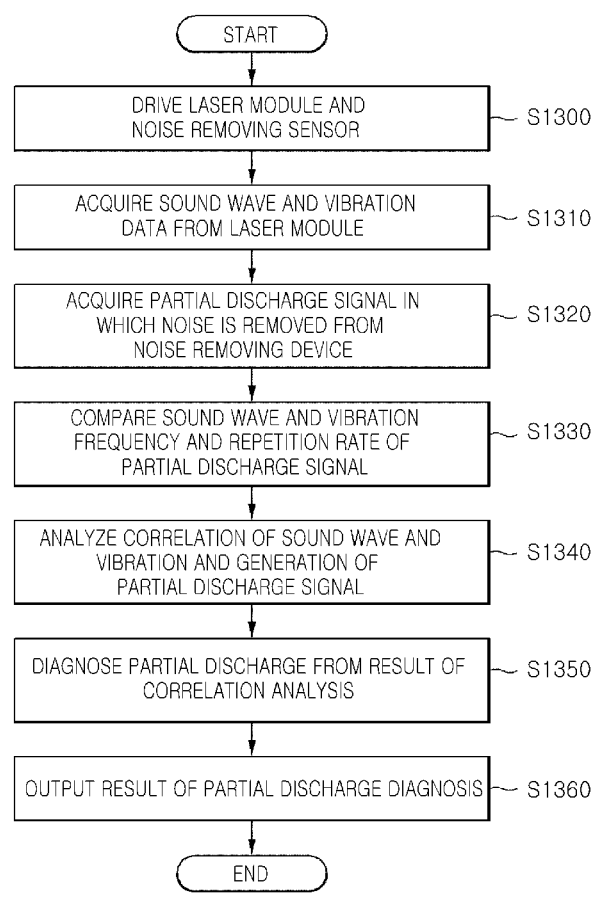
FIG. 17 is a flowchart illustrating an operation flow of a method of diagnosing partial discharge according to the present invention.

Here, the signal distribution data for each speed is used to diagnose the partial discharge signal in the device for diagnosing partial discharge, and more specifically, is used to generate the graph in FIG. 14, and based on the result, may be used in the operation of S1330 in FIG. 17 and the like.

Accordingly, the noise removing device 1200 outputs the partial discharge signal in which noise is removed in the operation of S1270 to the main body of the device for diagnosing partial discharge (S1280). In this case, the noise removing device 1200 may output the signal distribution data for each speed generated in the operation of S1260 to the main body of the device for diagnosing partial discharge in addition to the partial discharge signal. Needless to say, regardless of the operation of removing noise of the partial discharge signal, the signal distribution data for each speed generated in the operation of S1260 may be immediately output to the external device for diagnosing partial discharge upon generation along with alarm signal from the processor unit, an ACK signal in response to a control signal of the external device such as the device for diagnosing partial discharge, and the like.

FIG. 17 is a flowchart illustrating an operation flow of a method of diagnosing partial discharge according to the present invention.

As illustrated in FIG. 17, in order to diagnose partial discharge generated from the power device, the device for diagnosing partial discharge 1100 according to the present invention drives the laser module 1140 and the noise removing device 1200 (S1300).

Then, when the partial discharge is generated from the power device, the sound wave and vibration data is acquired from the laser module 1140 through each operation of FIG. 15 (S1310). The partial discharge signal in which noise is removed is acquired from the noise removing device 1200 through each operation of FIG. 16 (S1320).

In this case, the device for diagnosing partial discharge 1100 compares a sound wave vibration frequency of the sound wave and vibration data acquired in the operation of S1310 and the repetition rate of the partial discharge signal in which noise is removed acquired in the operation of S1320 (S1330).

In other words, in the operation of S1330, the sound wave vibration frequency is compared with at least one of a generation cycle, a time, and a phase of the partial discharge signal in which noise is removed. Therefore, the device for diagnosing partial discharge 1100 analyzes a correlation of the sound wave and vibration data and the partial discharge signal in which noise is removed from a comparison result of the operation of S1330 (S1340).

Based on the analysis result of the operation of S1340, when it is determined that there is a correlation between the sound wave and vibration data and the partial discharge signal in which noise is removed, the device for diagnosing partial discharge 1100 performs partial discharge diagnosis (S1350) and outputs a result of the partial discharge diagnosis (S1360).

The device and method for removing partial discharge noise, and the device and method for diagnosing partial discharge using the noise removing device according to the present invention have been described above with reference to the exemplary drawings. However, the present invention is not limited to the embodiments and drawings disclosed in this specification and may be applied within the scope and spirit of the invention.

The invention claimed is:

1. A device for removing partial discharge noise, comprising:
   a distributor configured to distribute a partial discharge signal detected through a partial discharge sensor into at least two signals when partial discharge is generated in a power device;
   a distributed signal processor configured to perform distributed signal processing on each of the partial discharge signals distributed by the distributor at reaction rates different from each other; and
   a differential signal processor configured to receive output signals obtained by performing distributed signal processing at reaction rates different from each other from the distributed signal processor, and remove noise included in the partial discharge signal based on a strength difference of the output signals.

2. The device of claim 1, wherein the distributed signal processor comprises:
   a high-speed circuit unit configured to perform high-speed signal processing on one signal among the distributed partial discharge signals using a high-speed logarithmic amplifier; and
   a low-speed circuit unit configured to perform low-speed signal processing on another signal among the distributed partial discharge signals using a low-speed logarithmic amplifier,
   wherein the high-speed logarithmic amplifier has a faster reaction rate than the low-speed logarithmic amplifier.

3. The device of claim 2, wherein the differential signal processor removes the noise included in the partial discharge signal by subtracting a peak value of a signal strength with respect to the output signal of the low-speed circuit unit from a peak value of a signal strength with respect to the output signal of the high-speed circuit unit.

4. The device of claim 2, wherein the distributed signal processor further comprises:
   a medium-speed circuit unit configured to perform medium-speed signal processing on another signal among the distributed partial discharge signals using a medium-speed logarithmic amplifier,
     wherein the medium-speed logarithmic amplifier has a slower reaction rate than the high-speed logarithmic amplifier, and a faster reaction rate than the low-speed logarithmic amplifier.

5. The device of claim 4, wherein, when a signal similar to the partial discharge signal is repeated at the same time zone, the differential signal processor removes the noise of the partial discharge signal based on a signal strength difference between the output signals of the high-speed logarithmic amplifier and the medium-speed logarithmic amplifier.

6. A method of removing partial discharge noise, comprising:
   when partial discharge is generated in a power device, distributing, by a distributor, a partial discharge signal detected through a partial discharge sensor into at least two signals;
   performing, by a distributed signal processor, distributed signal processing on each of the distributed partial discharge signals distributed by the distributor at reaction rates different from each other; and
   receiving, by a differential signal processor, output signals obtained by performing distributed signal processing at reaction rates different from each other from the distributed signal processor, and removing noise included in the partial discharge signal based on a strength difference of the output signals.

7. The method of claim 6, wherein, in the performing of the distributed signal processing, the distributed signal processor:
   performs high-speed signal processing on one signal among the distributed partial discharge signals using a high-speed logarithmic amplifier; and
   performs low-speed signal processing on another signal among the distributed partial discharge signals using a low-speed logarithmic amplifier,
   wherein the high-speed logarithmic amplifier has a faster reaction rate than the low-speed logarithmic amplifier.

8. The method of claim 7, wherein the removing of the noise comprises:
   subtracting, by the differential signal processor, a peak value of a signal strength with respect to the output signal of the low-speed logarithmic amplifier from a peak value of a signal strength with respect to the output signal of the high-speed logarithmic amplifier, and removing the noise included in the partial discharge signal.

9. The method of claim 7,
   wherein, in the performing of the distributed signal processing, the distributed signal processor performs medium-speed signal processing on another signal among the distributed partial discharge signals using a medium-speed logarithmic amplifier, the medium-speed logarithmic amplifier having a slower reaction rate than the high-speed logarithmic amplifier and a faster reaction rate than the low-speed logarithmic amplifier, and
   wherein, when a signal similar to the partial discharge signal is repeated at the same time zone, the removing of the noise comprises removing the noise of the partial discharge signal based on a strength difference between the output signals of the high-speed logarithmic amplifier and the medium-speed logarithmic amplifier.

* * * * *